(12) United States Patent  
Kressner

(10) Patent No.: US 8,661,597 B2  
(45) Date of Patent: Mar. 4, 2014

(54) BRUSH HEAD FOR A TOOTHBRUSH

(75) Inventor: Gerhard Kressner, Altenstadt (DE)

(73) Assignee: Braun GmbH, Kronberg (DE)

( * ) Notice: Subject to any disclaimer, the term of this patent is extended or adjusted under 35 U.S.C. 154(b) by 259 days.

(21) Appl. No.: 13/226,731

(22) Filed: Sep. 7, 2011

(65) Prior Publication Data

US 2012/0060309 A1     Mar. 15, 2012

(30) Foreign Application Priority Data

Sep. 9, 2010   (EP) ..................................... 10009364

(51) Int. Cl.  
    *A46B 9/04*      (2006.01)

(52) U.S. Cl.  
    USPC ........................................... 15/22.1; 15/22.2

(58) Field of Classification Search  
    USPC ................. 15/22.1, 22.2, 28, 167.1  
    See application file for complete search history.

(56) References Cited

U.S. PATENT DOCUMENTS

| | | | |
|---|---|---|---|
| 7,448,107 B2 * | 11/2008 | DePuydt et al. ................ | 15/22.1 |
| 2003/0084524 A1 | 5/2003 | Blaustein et al. | |
| 2007/0006403 A1 | 1/2007 | DePuydt et al. | |

FOREIGN PATENT DOCUMENTS

| | | |
|---|---|---|
| DE | 196 03 851 | 8/1997 |
| DE | 690 31 281 T2 | 3/1998 |
| EP | 0 537 465 A2 | 4/1993 |
| EP | 1 093 770 B1 | 4/2001 |
| JP | 2005-27762 | 2/2005 |
| WO | WO 2004/080330 | 9/2004 |

OTHER PUBLICATIONS

International Search Report for PCT/IB2011/053960 dated Dec. 27, 2011.

* cited by examiner

*Primary Examiner* — Shay Karls  
(74) *Attorney, Agent, or Firm* — John P. Colbert

(57) ABSTRACT

A brush head for an electric toothbrush is disclosed. The brush head includes a neck connectable to a handle of the electric toothbrush, and a bristle carrier pivotally supported by a pivot support at the neck about a pivot axis extending transverse to a longitudinal axis of the neck. The bristle carrier is provided with a drive joint connectable to a swivel element swiveling about a drive shaft axis substantially parallel to the longitudinal axis of the neck, the drive joint being radially spaced apart from the pivot axis of the bristle carrier and adapted to allow pivoting movement of the swivel element relative to the bristle carrier about a drive joint axis substantially parallel to the pivot axis of the bristle carrier, such that the pivot support provides for transverse movability of the bristle carrier relative to the pivot axis and/or of the pivot axis relative to the neck along a transverse axis extending transverse to the pivot axis, and that the drive joint is adapted to transmit driving forces of the swivel element to the bristle carrier in the direction of the transverse axis.

11 Claims, 3 Drawing Sheets

BRUSH HEAD FOR A TOOTHBRUSH

CROSS REFERENCE TO RELATED APPLICATIONS

This application claims the benefit of European Patent Convention Application No. 10009364.0, filed Sep. 9, 2010, the substance of which is incorporated by reference in its entirety herein.

FIELD OF THE INVENTION

The present disclosure relates to electric toothbrushes having a rotatably driven bristle field. More particularly, the present disclosure relates to a brush head for an electric toothbrush, the brush head having a rotatably driven bristle field.

BACKGROUND OF THE INVENTION

In order to enhance the cleaning efficiency of electric toothbrushes, it is desirable to move the bristle field along/about a plurality of axes. Such multi-axial movement of the bristle field achieves, inter alia, better, more intensive contact of the bristle tips to certain portions of the teeth difficult to reach otherwise. Furthermore, such multi-axial movement of the bristle field avoids that only some portions of the bristle field are moved relative to the brush head as it is the case with some prior art toothbrushes with a bristle field only rotating about an axis of rotation where the bristles close to the axis of rotation do not have much displacement, as shown in JP 2005-27762.

EP 1 093 770 B1 discloses an electric toothbrush with a rotary bristle supporting structure wherein the bristle carrier is supported in the neck of the brush head to be driven in rotary, especially oscillatory manner. The oscillating motion of the bristle carrier simultaneously induces, through a cam surface, a guided axial displacement which is a sort of rocking movement of the bristle carrier about an axis extending transverse to the toothbrush's plane of symmetry.

WO 2004-080330 discloses an electric toothbrush having a plurality of separate bristle fields which are driven to move about/along separate axes so that each bristle field has its own movement pattern. Consequently, different portions of the bristle field move into diverging directions, whereas each bristle field portion has only one axis of movement.

DE 690 31 281 T2 discloses an electric toothbrush having a pair of disc-shaped brushes with tufts which are inwardly oriented towards each other, wherein said brushes are rotated about an axis of rotation extending transverse to the longitudinal axis of the toothbrush. Between the two disc-shaped brushes, there are two bar-shaped bristle fields executing a linear oscillating movement.

Furthermore, DE 196 03 851 shows an electric toothbrush having a disc-shaped bristle carrier which is rotated about an axis of rotation extending transverse to the toothbrush's longitudinal axis and thus substantially parallel to the tufts anchored to said bristle carrier. In addition to such rotatory movement, the bristle carrier is axially oscillated along the longitudinal axis of the toothbrush. To achieve the rotatory movement and the linear movement of the bristle carrier, the drive train includes a drive shaft extending between the handle and the head of the toothbrush, which drive shaft is driven to execute a rotation about its longitudinal axis and additionally a linear oscillating movement along its longitudinal axis. Such multi-axial movement of the drive shaft necessitates a rather complicated transmission and gearing between the electric motor and the handle and the drive shaft.

EP 0 537 465 A2 shows an electric toothbrush with a pair of bristle carriers mounted to the brush head. Said bristle carriers are also rotated about a transverse axis substantially parallel to the tufts mounted to the bristle carriers, and in addition, oscillated along the longitudinal axis of the toothbrush. These two different movements of the bristle carriers are achieved with a drive shaft which executes only a linear reciprocating movement basically along the longitudinal axis of the toothbrush. More particularly, said drive shaft is connected at its one end to a rotating wheel so that the other end of the drive shaft reciprocates like the connecting rod of a combustion engine's connecting rod connecting the piston to the crankshaft. The other end of the drive shaft is connected to the bristle carriers to move such bristle carriers along the toothbrush's longitudinal axis in a reciprocating manner. To additionally provide for rotation of said bristle carriers, the bristle carriers are provided with pinions in engagement with a toothed rack mounted to the brush head. Such transmission is rather complicated and makes the brush head rather bulky.

It is a desire to provide an improved electric toothbrush and an improved brush head for such toothbrush which avoid disadvantages of the prior art and provide improvement thereof. Particularly it is a desire to provide a multi-axial bristle carrier movement for better cleaning efficiency without complicated transmission and gearing in the drive train and achieving a slim, space saving configuration.

SUMMARY OF THE INVENTION

According to one embodiment, a brush head for an electric toothbrush is provided. The brush head includes a neck connectable to a handle of the electric toothbrush, and a bristle carrier pivotally supported by a pivot support at the neck about a pivot axis extending transverse to a longitudinal axis of the neck. The bristle carrier is provided with a drive joint connectable to a swivel element swiveling about a drive shaft axis substantially parallel to the longitudinal axis of the neck, the drive joint being radially spaced apart from the pivot axis of the bristle carrier and adapted to allow pivoting movement of the swivel element relative to the bristle carrier about a drive joint axis substantially parallel to the pivot axis of the bristle carrier, such that the pivot support provides for transverse movability of the bristle carrier relative to the pivot axis and/or of the pivot axis relative to the neck along a transverse axis extending transverse to the pivot axis, and that the drive joint is adapted to transmit driving forces of the swivel element to the bristle carrier in the direction of the transverse axis.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

Figure 1:
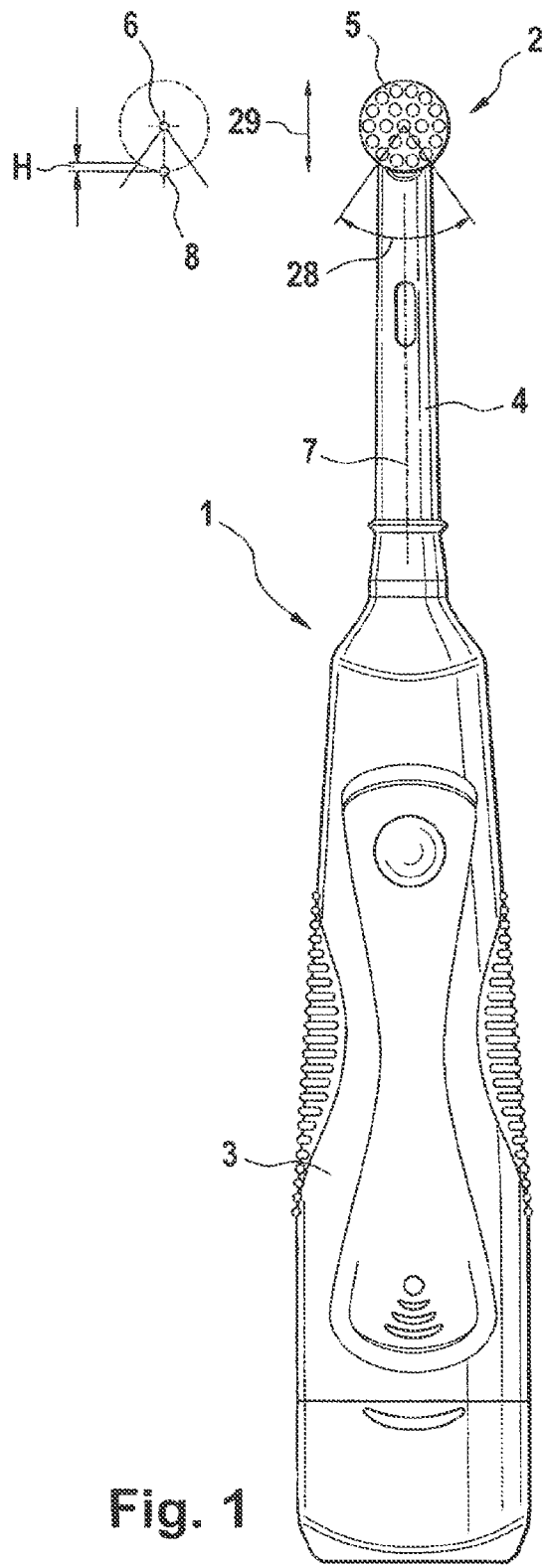
FIG. 1 is a plain view of an electric toothbrush according to according to embodiments shown and described herein.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

According to the present disclosure, a brush head for an electric toothbrush is provided. In order to achieve multi-axial movement of the bristle carrier, the pivot support of the bristle carrier is provided with an additional degree of freedom. In one embodiment, a swivel element swiveling about a drive shaft axis and a drive joint connecting the swivel element to a bristle carrier are adapted to transmit driving forces in the direction of the additional degree of freedom. The swiveling movement of the swivel element about the drive shaft axis is sufficient to make the bristle carrier pivot about the pivot axis and reciprocate along the transverse axis. In one embodiment, the pivot support of the bristle carrier provides for transverse movability thereof relative to the pivot axis and/or of the pivot axis relative to the neck along a transverse axis extending transverse to the pivot axis. The drive joint is adapted to transmit driving forces of the swivel element to the bristle carrier in the direction of the transverse axis. Thus, multi-axial movement of the bristle carrier is effected without complicated and space consuming gearings such as toothed rack and without necessitating the drive shaft between the handle and the brush head to execute multi-axial movements. The drive shaft may move about one axis only wherein such simple movement is translated into a multi-axial movement of the bristle carrier.

The additional degree of freedom of the bristle carrier may be achieved in different ways and by different pivot support structures. In accordance with one embodiment, the pivot support may be provided with guiding means for slidably guiding the bristle carrier at the pivot axis along the transverse axis, wherein the guiding means may include an elongated, groove-shaped recess for slidably receiving the pivot axis, the recess extending along the transverse axis and being formed in the bristle carrier. The elongated groove in the bristle carrier may have a width substantially corresponding to the diameter of the pivot axis, whereas the length of the elongated groove is considerably larger than the pivot axis "diameter". Thus, the bristle carrier may pivot about the pivot axis and additionally slide relative to the pivot axis in the direction of the longitudinal axis of the elongated groove. When the bristle carrier is provided with such elongated recess, the pivot axis may be secured rigidly to the neck so the pivot axis may not change its position and angular orientation. Nevertheless, it is possible that the pivot axis itself may rotate about its longitudinal axis, but this is not necessary, since the bristle carrier may pivot relatively to the pivot axis, so the pivot axis may be secured to the neck completely.

Alternatively or in addition to such slidably guiding of the bristle carrier at the pivot axis, the pivot axis may be slidably guided at the neck to be movable along said transverse axis and to allow the bristle carrier to move along the transverse axis. For example, the neck of the brush head could be provided with an elongated, in particular groove-shaped recess for slidably receiving the pivot axis, wherein the pivot axis could be secured to the bristle carrier at a fixed position in a fixed angular orientation so that the bristle carrier together with the attached pivot axis could slide in the elongated groove in the neck and addition rotate relative to the neck about the pivot axis.

According to one embodiment, the transverse axis along which the bristle carrier may move relative to the neck may extend substantially parallel to the longitudinal axis of the toothbrush and/or parallel to the drive shaft axis about which the swivel element swivels. Consequently, the bristle field may move towards and away from the handle of the toothbrush, in addition to its rotational movement about the pivot axis extending transverse to the longitudinal axis of the toothbrush. Such combination of movements provides for improved cleaning efficiency, in particular at the interdental portions of the teeth as well as at the portions neighboring the gingival.

In order to achieve relatively large amplitudes of the oscillation movements of the bristle carrier with additional amplitudes of the oscillating movement of the swivel element, the geometry of the drive train may be chosen such that the connecting point between the swivel element and the bristle carrier is positioned in a sector of the bristle carrier that opens towards the handle of the toothbrush when the bristle carrier is in its center position from which it rotatively oscillates to opposite directions. In other words, the drive joint connecting the swivel element to the bristle carrier is, in one embodiment, positioned between the pivot axis and the neck portion connecting to the handle when the bristle carrier is, in terms of its pivoting movement about the pivot axis, in a centered position. In particular, when viewed in the direction of the pivot axis, a line connecting the drive joint with a pivot axis of the bristle carrier may extend substantially parallel to the longitudinal axis of the neck.

In order to avoid uncontrolled tumbling of the bristle carrier due to the additional degree of freedom, the pivot support structure includes tumble prevention means that holds the bristle carrier in a defined angular orientation when pivoting about the pivot axis. In accordance with one embodiment, the tumbling prevention means may include a pair of guiding elements provided at the neck and the bristle carrier, respectively, the guiding elements being a sliding engagement with each other and adapted to allow movement of the bristle carrier relative to the neck in plane perpendicular to the pivot axis only. Consequently, the bristle carrier is kept in the desired angular orientation despite the aforementioned elongated groove in which the pivot axis is received.

According to one embodiment, the guiding element of the tumble prevention means may include a projection slidably received in a in particular groove-shapes recess, wherein the recess is provided in the bristle carrier, whereas the projection is insertable into the recess through a through-hole provided in the neck from an outer surface thereof. Such configuration facilitates easy mounting of the brush head and the bristle carrier. Nevertheless, according to an alternative embodiment, the bristle carrier may be provided with a radially extending projection received in a corresponding recess formed in the neck to hold the bristle carrier in the desired angular orientation when pivoting about the pivot axis. However, in one example, a holding pin insertable through a wall of neck from an outside thereof and projecting into a groove-shaped recess in the bristle carrier to prevent tumbling thereof is provided.

In order to effect the additional movement of the bristle carrier along the transverse axis, the swivel element is held in a fixed axial position relative to the neck at which the bristle carrier is supported. Contrary to prior art embodiments having such swivel elements for driving the bristle carrier, the swivel element cannot move in a direction parallel to the drive shaft axis, but is maintained in a fixed axial position so that the swivel element moves along a circular path along the pivot axis. The drive shaft supporting the swivel element may not either move along the longitudinal axis of the neck so the axial position of the swivel element is fixed relative to the neck when in functional engagement. Such axial fixed support of the swivel element ensures a maximum axial reciprocating movement of the bristle carrier even when the amplitude of the swiveling oscillation of the swivel element is small. In one embodiment, the pivot joint between the swivel element and the bristle carrier is adapted to not allow axial movement of the swivel element relative to the bristle carrier in the direction of the longitudinal axis of the neck. In one embodiment, the pivot joint may connect the swivel element to the bristle carrier substantially without any play in the direction of the drive shaft axis and/or the longitudinal axis of the neck. Consequently, any angular displacement of the swivel element and consequently any rotational displacement of the bristle carrier is translated into a linear displacement of the bristle carrier.

The holding means for holding the swivel element relative to the neck in the axial direction of the drive shaft axis may include a rotatable support for the drive shaft at the neck, the rotatable support being provided with an axial supporting element for axially supporting the drive shaft at the neck in the direction of the drive shaft axis. In one embodiment, the axial supporting element holds the drive shaft in an axial fixed position at the neck substantially without play.

The axial support of the drive shaft can be designed in different ways. According to an embodiment, the axial supporting element may include a locker for locking the drive shaft in an axial fixed position at the neck. For example, a locking pin can be inserted transversely into a recess such as an angular groove of the drive shaft, the locking pin being received in a bore or similar recess extending transversely in the neck.

As mentioned previously, the drive joint between the swivel element and the bristle carrier does not provide for axial play in the direction of the drive shaft axis. However, the drive joint may be adapted to allow displacement of the swivel element relative to the bristle carrier in a direction parallel to the pivot axis of the bristle carrier. Since the swiveling movement of the swivel element about the drive shaft axis includes a vertical component, in particular when oscillating with a larger amplitude towards the dead end points of the swiveling oscillation, such movability of the swivel element relative to the bristle carrier in a direction parallel to the pivot axis compensates for such vertical component of the swiveling movement. In accordance with one embodiment, the drive joint may include supporting means such as linear guiding means for slidably guiding an end piece of the swivel element at the bristle carrier in a direction parallel to the pivot axis thereof. For example, the guiding means may include a bore-shaped recess for slidably receiving the stud-shaped end piece of the swivel element slidable in the longitudinal direction of the bore-shaped recess and rotatable about the longitudinal direction.

Alternatively or in addition to such slidable support of the swivel element at the bristle carrier, the pivot support of the bristle carrier at the neck may provide for such compensation of the vertical component of the swiveling movement of the swivel element. For example, the pivot axis may be slidably received in a respective recess in the bristle carrier to allow movement of the bristle carrier along the pivot axis that means up and down substantially parallel to the bristle tufts. Consequently, the aforementioned vertical component of the swiveling movement of the swivel element may be utilized to create to a sort of chisel movement of the bristle tufts, thereby improving removal of plaque and cleaning of the interdental spaces.

Figure 2:
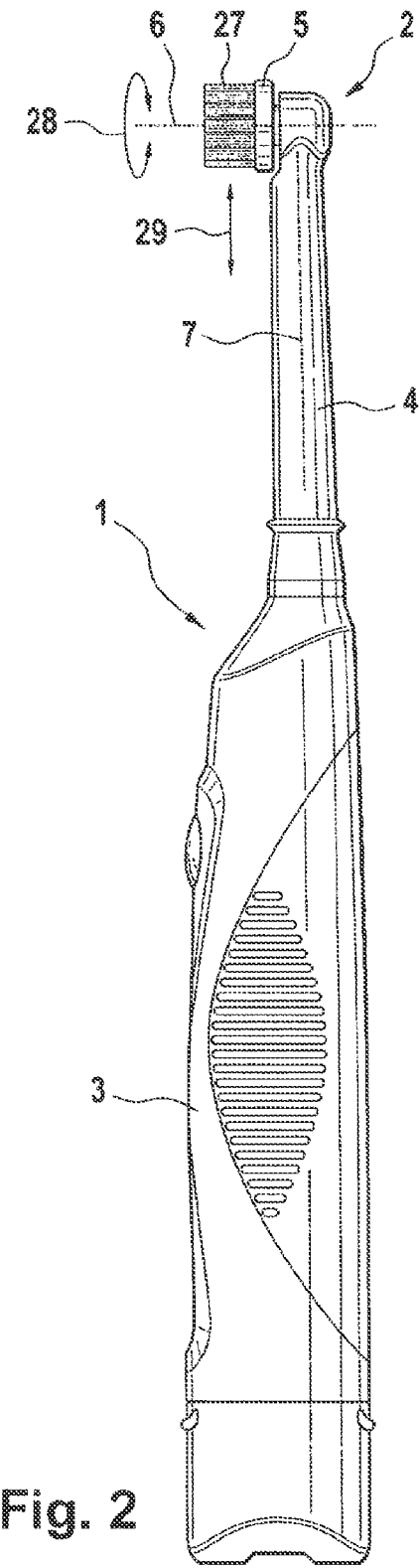
FIG. 2 is a side view of the electric brush of FIG. 1.

Beginning with FIGS. 1 and 2, an exemplary electric toothbrush 1 includes a brush head 2 having an elongated, substantially tube-shaped neck 4 which is releasably connected to a handle 3. The handle 3 includes an electric power source such as batteries, an electric motor powered by the power source and control means such as a start/stop button for controlling the drive unit.

The brush head 2 supports a bristle carrier 5 which in the shown embodiment may have a substantially plate-shaped and/or cylindrical carrier section to which a plurality of cleaning elements such as bristle tufts, elastomeric fingers or interdental rods etc. are mounted as it is known in the art. According to the embodiments of FIGS. 1 and 2, a bristle field 27 is mounted to the bristle carrier 5.

As indicated by the arrows 28 and 29 in FIGS. 1 and 2, two different motions can be induced to the bristle carrier 5 and consequently the bristle field 27 attached thereto. On the one hand, the bristle carrier 5 is oscillated in a rotating manner through an angle of plus-minus alpha about pivot axis 6 which substantially extends transverse to the longitudinal axis 7 of the neck 4 and substantially parallel to the longitudinal axis of the bristle tufts. The longitudinal axis 7 of the neck 4 basically corresponds to the longitudinal axis of the entire toothbrush 1. Secondly, the bristle carrier 5 is oscillated in a reciprocating manner along a transverse axis 13 extending substantially in parallel to the aforementioned longitudinal axis 7 as indicated by arrow 29.

The two motions represented by arrows 28 and 29 are created by a drive train connecting the aforementioned motor in the handle 3 to the bristle carrier 5 and extending through the interior of neck 4. As FIG. 3 shows, the drive train 30 includes a drive shaft 10 oscillating in a rotating manner about drive shaft axis 11 which substantially extends in parallel to the longitudinal axis 7 of the neck 4.

Figure 3:
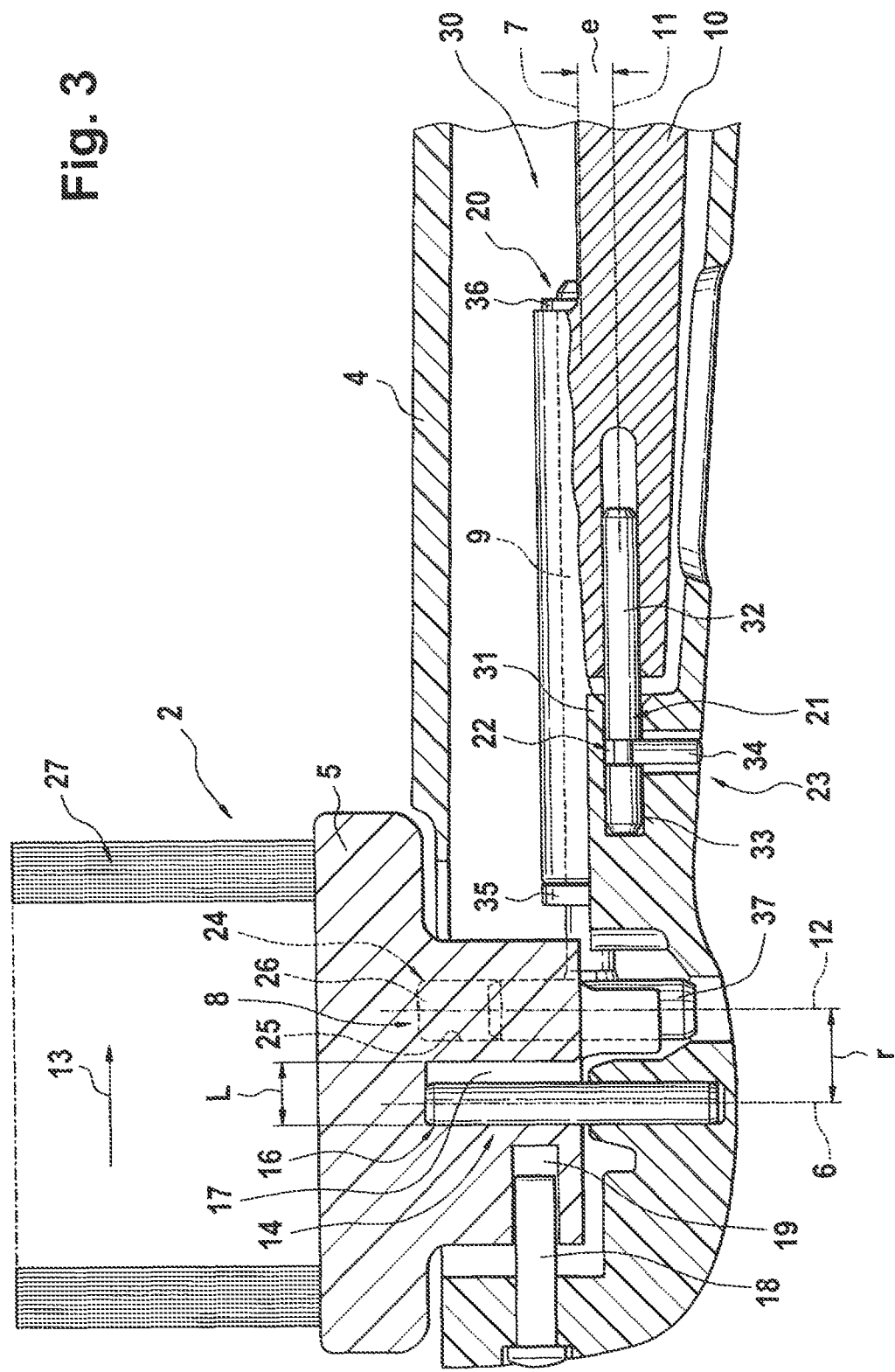
FIG. 3 is a sectional view of the brush head of toothbrush of the preceding figures showing the pivot support structure of the bristle carrier and the engagement of the bristle carrier with the swivel element of the drive shaft, wherein the bristle carrier and the swivel element are shown in a position where the bristle carrier is in a position displaced towards the handle of the toothbrush.

As can be seen in FIG. 3, the drive shaft 10 is rotatably supported at the neck 4 having a supporting portion 31 formed by a step-like projection of the inner side of the wall of the neck 4. At the supporting portion 31, a rotatable support 21 is provided for said drive shaft 20, wherein the rotatable support 21 includes—in the shown embodiment—a support pin 32 rigidly connected to the drive shaft 10 and rotatably received in a bore-shaped recess 33 in the supporting portion 31 of the neck 4. The support pin 32 which may be rigidly fixed to the drive shaft 10 may rotate in said recess 33, however, it may be axially fixed so that the drive shaft 10 is held in an axially fixed position relative to the neck 4. As shown in FIG. 3, the support pin 32 may be locked axially by means of a locking pin 34 extending transversely to the support pin 32 which has an annular groove receiving the locking pin 34. The locking pin 34 may be inserted in a transverse bore in the supporting portion 31 of the neck 4. Thus, the locking pin 34 and the annular groove in the circumference of the support pin 32 form an axial supporting element 22. Instead of extending through the support pin 32, the locking pin 34 could be arranged further down the neck 4 at a position, where the locking pin 34 would extend through a transverse bore in the neck 4 and into an annular groove provided in the drive shaft 10 to axially fix the drive shaft 10 relative to the neck 4. This would avoid providing an annular groove in the thin support pin 32.

Figure 4:
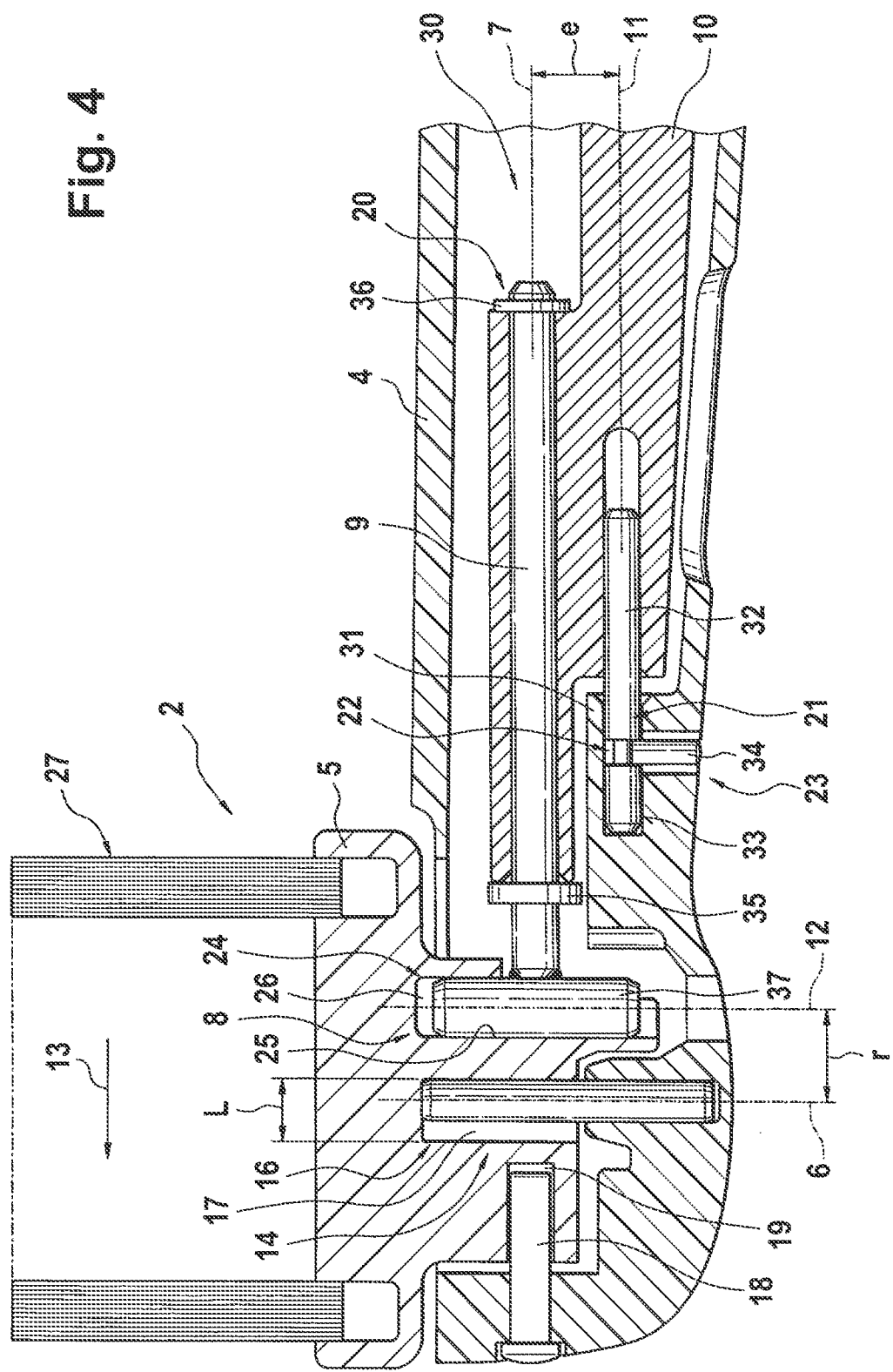
FIG. 4 a sectional view of the brush head similar to FIG. 3, wherein the bristle carrier is shown in a position displaced away from the handle of the toothbrush.

The drive shaft 10 which is supported axially fixed, but rotatable about the drive shaft axis 11 supports a swivel element 9 which is positioned radially spaced from the drive shaft axis 11 so that the swivel element 9 is eccentric to the drive shaft axis 11 by a distance e (FIG. 4 shows the situation where the drive shaft 10 is in a centered position, while FIG. 3 shows the situation where the drive shaft 10 is rotated inside the neck). Consequently, the swivel element 9 swivels about drive shaft axis 11 in an oscillating manner when the drive shaft 10 is oscillated in a rotating manner.

In the shown embodiment, the swivel element 9 is supported at the drive shaft 10 in a rotatable manner. More particularly, the swivel element 9 may rotate about the longitudinal axis of the swivel element 9 extending in parallel with the drive shaft axis 11. In the shown embodiment, this rotating motion of the swivel element 9 is the only motion that is available to the swivel element 9 relative to the drive shaft 10. In particular, the swivel element 9 is held relative to the drive shaft axis 11 in a fixed axial position in the direction of the drive shaft axis 11, that means the swivel element 9 may not move relative to the drive shaft 10 and/or the neck 4 from left to right in FIG. 3, irrespective of the rotatory position of the drive shaft 10. As shown by FIG. 3, the swivel element 9 may be formed as a pin, wherein radial projections 35 and 36 hold the pin in axial direction at the drive shaft 10.

An end portion of the swivel element 9 is connected to the bristle carrier 5 at a drive joint 8. The drive joint 8 is adapted to prevent any movement of the swivel element 9 relative to the bristle carrier 5 in directions perpendicular to the pivot axis 6 of the bristle carrier 5 and/or in the direction of the drive shaft axis 11. In another embodiment, the drive joint 8 allows for motion of the bristle carrier 5 relative to the swivel element 9 along and about a drive joint axis extending parallel to the pivot axis 6. More particularly, the swivel element 9 may rotate about the drive joint axis 12 relative to the bristle carrier 5. Furthermore, the swivel element 9 may slide relative to said bristle carrier 5 along the drive joint axis 12.

To allow such motions on the one hand and to prevent any relative motion transverse to the pivot axis, the swivel element 9 may be provided with a stud 37 at one end, which stud is received within a bore-shaped recess 26 formed in the bristle carrier 5. The stud 37 received in the recess 26 thus forms a sort of guiding means 25 slidably guiding the end piece of the swivel element at said bristle carrier in a direction parallel to the pivot axis 6 and, at the same time a sort of rotatable support. Thus, the drive joint 8 has two degrees of freedom along and about the drive joint axis 12, but whereas no transverse motion of the swivel element 9 relative to the bristle carrier 5 in a direction transverse to the pivot axis 6 of the bristle carrier 5 is allowed.

As shown by FIGS. 3 and 4, the bristle carrier 5 itself is supported at the neck 4 by a pivot support 14 having two degrees of freedom allowing for a pivoting movement about the pivot axis 6 and in addition, a linear movement along a transverse axis 13, extending transverse to the pivot axis 6. More particularly, the transverse axis 13 extends substantially in parallel to the longitudinal axis 7 of the neck 4.

In the embodiment of FIGS. 3 and 4, the pivot support 14 includes a pivot axis 6 rigidly attached to the neck 4 and extending in a direction substantially perpendicular to the longitudinal axis 7 of neck 4. As can be seen in FIG. 3, the pivot axis 6 is formed by a pivot pin projecting from the bottom of a bristle carrier recess of the neck 4 in which recess the lower part of the bristle carrier 5 is received.

The cooperating part of the pivot support 14 is formed by an elongated, groove-shaped recess 17 in the bottom side of the bristle carrier 5 in which recess 17 the aforementioned pivot axis 6 is received. The elongated recess 17 has a width basically corresponding to the diameter of the pivot axis 6, whereas the length L of the recess 17 is significantly longer than the pivot axis "diameter". More particularly, the length L is sufficient so as to allow the bristle carrier 5 to move forward and backward when oscillated in pivoting manner about pivot axis 6 due to the driving action if the swivel element 9. The linear movement of the bristle carrier 5 along the transverse axis 13 is determined by the geometry of the drive train 30, in particular the eccentricity e of the swivel element 9 relative to the drive shaft axis 11, the amplitude of the rotative oscillation of the drive shaft 10 and the distance r of the drive joint 8 from the pivot axis 6.

When viewed in the direction of the pivot axis 6 as shown in FIG. 1, the bristle carrier 5 executes a rotative oscillation so the drive joint 8 moves along an angular path about the pivot axis 6. The angular path, the length of which is determined by the aforementioned parameters, has a certain height H defined in the direction of the longitudinal axis 7 of the neck 4, as can be seen in FIG. 1. In order to allow the respective linear displacement of bristle carrier 5, the aforementioned elongated recess 17 receiving the pivot axis 6 has a length L corresponding to 100% to 150% of the height H plus the diameter of the pivot axis 6.

In order to avoid tumbling of the bristle carrier 5 which would be possible because of the elongated shape of the recess 17 receiving the pivot axis 6, the pivot support 14 of the bristle carrier 5 includes tumble prevention means holding the bristle carrier 5 in a desired angular orientation irrespective of the rotatory and axial position thereof. In the shown embodiment, the tumble prevention means includes a pair of guiding elements provided at the neck 4 and the bristle carrier 5 respectively, the guiding elements being in sliding engagement with each other and adapted to allow movement of the bristle carrier 5 relative to the neck 4 in a plane perpendicular to the pivot axis 6 only.

More particularly, as shown in FIG. 3, the guiding elements may include a projection 18 projecting from the wall of neck 4 into the bristle carrier receiving recess in the neck 4 and, on the other hand, a slot-like recess formed in the circumferential side of the bristle carrier 5, see for example, FIG. 3. The recess 19 has a width—the extension parallel to the pivot axis 6—substantially corresponding to the diameter of the projecting pin 18. As can be seen in FIG. 3, it is preferred that the projecting pin is inserted into the recess in the bristle carrier 5 through a through-hole in the neck 4 from an outer surface thereof. This facilitates easy mounting of the brush head 2.

As shown by a comparison of FIGS. 3 and 4, the bristle carrier 5 reciprocates in axial direction parallel to the longitudinal axis 7 when pivoted about pivot axis 6, what is possible due to the elongated shape of recess 17 and the axially fixed position of swivel element 9 and the axially rigid structure of drive joint 8. As can be seen in FIG. 3, the drive joint 8 is radially spaced apart from the pivot axis 6 by the distance r. When the drive shaft 10 is in its centered position, that means the angular position in the middle of the rotative oscillation, the drive joint 8 is positioned in the toothbrush's plane of symmetry containing the longitudinal axis 7 of the neck 4. As can be seen from FIG. 3, the drive joint 8 is positioned on the side of the bristle carrier 5 facing the handle 3.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A brush head for an electric toothbrush, comprising:
a neck connectable to a handle of the electric toothbrush, and a bristle carrier pivotally supported by a pivot support at the neck about a pivot axis extending transverse to a longitudinal axis of the neck, wherein the bristle carrier is provided with a drive joint connectable to a swivel element swiveling about a drive shaft axis substantially parallel to the longitudinal axis of the neck, the drive joint being radially spaced apart from the pivot axis of the bristle carrier and adapted to allow pivoting movement of the swivel element relative to the bristle carrier about a drive joint axis substantially parallel to the pivot axis of the bristle carrier, such that the pivot support provides for transverse movability of the bristle carrier relative to the pivot axis and/or of the pivot axis relative to the neck along a transverse axis extending transverse to the pivot axis, and that the drive joint is adapted to transmit driving forces of the swivel element to the bristle carrier in the direction of the transverse axis; and wherein the pivot axis is secured to the neck at a fixed position in a fixed angular orientation and tumble prevention means are provided for preventing the bristle carrier from tumbling, the tumble prevention means projecting from an outer surface of a wall of the neck through a through-hole and into the bristle carrier in a plane perpendicular to the pivot axis.

2. The brush head according to claim 1, wherein the pivot support is provided with guiding means for slidably guiding the bristle carrier at the pivot axis along the transverse axis, the guiding means in particular including an elongated, groove-shaped recess for slidably receiving the pivot axis, the recess extending along the transverse axis and being formed in the bristle carrier.

3. The brush head according to claim 2, wherein the groove-shaped recess in the bristle carrier for receiving the pivot axis has a length L corresponding to the sum of the pivot axis diameter d and 100% to 150% of the height H of the angular path of the pivot joint around the pivot axis.

4. The brush head according to claim 1, wherein the transverse axis extends substantially parallel to the longitudinal axis of the neck.

5. The brush head according to claim 1, wherein the drive joint is positioned at the bristle carrier such that, when the bristle carrier is, in terms of its pivoting movement about the pivot axis, in a pivotally centred position, a line connecting the drive joint with the pivot axis of the bristle carrier extends substantially parallel to the longitudinal axis of the neck when viewed in the direction of the pivot axis.

6. The brush head according to claim 1, wherein the tumbling prevention means include a pair of guiding elements provided at the neck and the bristle carrier, respectively, the guiding elements being in sliding engagement with each other and adapted to allow movement of the bristle carrier relative to the neck in a plane perpendicular to the pivot axis.

7. The brush head according to claim 6, wherein the guiding elements include a projection slidably received in a substantially groove-shaped recess, wherein the recess is provided in the bristle carrier and the projection is insertable into the recess through the through-hole.

8. The brush head according to claim 1, wherein holding means are provided for holding the swivel element relative to the neck in a fixed axial position in the direction of the drive shaft axis, the holding means in particular including a rotatory support for the drive shaft at the neck, the rotatory support being provided with an axial supporting element for axially supporting the drive shaft at the neck in the direction of the drive shaft axis.

9. The brush head according to claim 8, wherein the axial supporting element includes a locking pin for locking the drive shaft in an axially fixed position at the neck.

10. The brush head according to claim 1, wherein the drive joint is provided with supporting means adapted to allow displacement of the swivel element relative to the bristle carrier in a direction parallel to the pivot axis of the bristle carrier.

11. The brush head according to claim 10, wherein the supporting means of the drive joint includes a linear guiding means for slidably guiding an end piece of the swivel element at the bristle carrier in a direction parallel to the pivot axis thereof, the guiding means in particular including a bore-shaped recess for slidably receiving the stud-shaped end piece of the swivel element slidable in the longitudinal direction of the bore-shaped recess and rotatable about the longitudinal direction.

* * * * *